(12) United States Patent
Feder (10) Patent No.: US 6,758,811 B1
(45) Date of Patent: Jul. 6, 2004

(54) INTERNET SERVER APPARATUS, METHOD AND DEVICE FOR IMPLEMENTING EMERGENCY INFORMATION INSTRUCTIONS

(75) Inventor: David L. Feder, Irvine, CA (US)

(73) Assignee: Safetymate, Inc., Irvine, CA (US)

( * ) Notice: Subject to any disclaimer, the term of this patent is extended or adjusted under 35 U.S.C. 154(b) by 442 days.

(21) Appl. No.: 09/805,339

(22) Filed: Mar. 12, 2001

Related U.S. Application Data (60) Provisional application No. 60/188,641, filed on Mar. 10, 2000.

(51) Int. Cl.[7] .................................................. A61B 5/00
(52) U.S. Cl. ........................ 600/300; 364/400; 705/3; 369/32; 369/41; 128/920
(58) Field of Search ........................ 600/300; 128/920; 364/400, 413.01, 413.02, 413.03; 705/3; 434/321, 322, 323; 369/32, 41; 395/202, 203, 237, 241, 603, 604, 605, 606

(56) References Cited

U.S. PATENT DOCUMENTS

| | | |
|---|---|---|
| 3,845,250 A | 10/1974 | O'Brien |
| 4,303,395 A | 12/1981 | Bower |
| 4,569,026 A | 2/1986 | Best |
| 4,583,524 A | 4/1986 | Hutchins |
| 4,588,383 A | 5/1986 | Parker et al. |
| 4,677,552 A | 6/1987 | Sibley, Jr. |
| 5,025,374 A | 6/1991 | Roizen et al. |
| 5,059,126 A | 10/1991 | Kimball |
| 5,086,391 A | 2/1992 | Chambers |
| 5,088,037 A | 2/1992 | Battaglia |
| 5,106,097 A | 4/1992 | Levine |
| 5,185,857 A | 2/1993 | Rozmanith et al. |
| 5,274,560 A | 12/1993 | LaRue |
| 5,521,812 A | 5/1996 | Feder et al. |
| 5,668,954 A | 9/1997 | Feder et al. |
| 6,304,788 B1 * | 10/2001 | Eady et al. .................. 600/300 |
| 6,319,207 B1 * | 11/2001 | Naidoo ....................... 600/300 |
| 6,398,729 B1 * | 6/2002 | Levinson .................... 600/300 |
| 6,443,890 B1 * | 9/2002 | Schulze et al. ............. 600/300 |
| 6,544,198 B2 * | 4/2003 | Chong et al. ............... 600/300 |
| 6,602,191 B2 * | 8/2003 | Quy ............................ 600/300 |

* cited by examiner

Primary Examiner—Henry Bennett
Assistant Examiner—Fadi H. Dahbour
(74) Attorney, Agent, or Firm—Orrick, Herrington & Sutcliffe LLP (57) ABSTRACT

There is disclosed herein an Internet server apparatus, method and device for implementing emergency information instructions. The instructions comprise a program of a plurality of steps and can be in the form of a virtual implementation through use of a web page that includes representations of a virtual emergency information apparatus or, alternatively, in the form of a physical portable device. Indicators are provided in the form of lights or a numerical display to indicate the completion of sequential steps in the program so as to aid the user in knowing how many steps will be necessary and to indicate the completion of each step.

34 Claims, 6 Drawing Sheets

INTERNET SERVER APPARATUS, METHOD AND DEVICE FOR IMPLEMENTING EMERGENCY INFORMATION INSTRUCTIONS

This application claims the benefit of Provisional application Ser. No. 60/188,641, filed Mar. 10, 2000.

BACKGROUND OF THE INVENTION

1. Field of the Invention

The present invention relates generally to the Internet and related devices and, more particularly, to an Internet web server that provides web documents, or a physical device, that relate to the interactive provision of instructional information particularly in medical and other emergency situations.

2. Description of Related Art

In any emergency operation, such as in the rescue of an unconscious victim, it is of paramount importance for the individuals involved to take the proper actions as soon as possible. Normally, if proper rescue operations are applied to a victim, the chance of survival or recovery of the victim are much improved. In order to carry out many rescue operations effectively, the rescuer must follow the steps set forth in any of the standard medical rescue manuals. The proper procedure is generally based upon the particular condition of the victim.

Standard rescue procedures are well developed in the medical field and are beyond the scope of this disclosure, except so far as may be necessary to explain the nature and applications of the present concepts. Studies have shown that even amongst professional rescue operators such as paramedic, firemen and nurses, relatively few people can remember the proper rescue sequence or procedure precisely. This is further complicated because the "standard" procedures frequently change as they are refined and new methodologies are introduced.

Even more importantly, a paramedic, fireman, nurse or other emergency medical technician is generally not available in the critical initial moments of an emergency. Rather, lay rescuers, i.e., ordinary individuals, generally discover emergencies, and these people are responsible for both initiating the proper procedures and determining whether additional assistance from professionals is necessary.

In general, the standard procedures have become more complex, and more procedures have been created for a growing number of emergencies. As procedures become more and more complex, potential rescuers have more and more difficulty in obtaining familiarity with them and memorizing them.

Moreover, the ability of a rescuer to recall and employ the proper emergency procedure is further hampered by the chaotic circumstances typically surrounding an emergency situation.

The prior art has seen varied approaches to the handling of emergency instructions or to the use of audible instructions. The prior art systems have included use of instruction booklets having indices in which the particular emergency has to be located; then pages flipped to locate the emergency; and read step by step while trying to perform the emergency with one hand and constantly going back to reread the instructions. The prior art also has included sophisticated computer instructions that are activated by a particular code on a telephone to give a caller instructions as to how to fill out a bank deposit, how to call a particular bit of information regarding insurance policies or the like.

Attempts have been made to provide devices to assist in providing emergency information to ensure that a rescuer performs the rescue operation properly. However, most of these have been devices dedicated to just one type of emergency—cardiopulmonary resuscitation (CPR). One of such devices is shown in U.S. Pat. No. 4,451,158 to Selwyn et al. Selwyn's device is in the form of a timer with various coded pattern displays at predetermined time intervals to indicate various stages in the rescue operation. The main drawback of the device is that confusion may still arise for the rescuer to memorize which procedural step is related to which code.

Another device, such as that shown in U.S. Pat. No. 4,588,383 to Parker et al., provides voice instructions solely for the rescuer to carry out the CPR rescue operation. Other portable CPR-prompting devices have been disclosed in U.S. Pat. No. 4,588,383 to Parker et al., U.S. Pat. No. 4,583,524 to Hutchins and U.S. Pat. No. 5,088,037 to Battaglia.

An emergency audible instruction apparatus for a fire extinguisher is disclosed in U.S. Pat. No. 4,303,395 to Bower. Such a device provides audible instructions which instruct a user in handling a fire emergency. The device is activated automatically when the fire extinguisher is removed from its base. Bower suggests that a device embodiment storing multiple instructions may be included with a dial selector for selecting a particular emergency. However, unlike the CPR-prompting devices, the Bower device is not portable and suggests purely mechanical means for providing a portable solution.

A generalized manual key operated message generator is described in U.S. Pat. No. 3,845,250 to O'Brien. However, this device is not portable nor adapted for emergency use. To retrieve a message, the user presses a series of keys to assemble a complete message upon prerecorded parts.

U.S. Pat. No. 5,086,391 describes a medical alert system for domestic use comprising two major components, a device worn about the neck and a home computer. The device worn about the neck and the home computer reciprocally communicate with one another to provide the wearer of the device, as well as an attendant of the device, both instructions for care and a method to call for emergency help. The home computer contains an audio synthesizer and a voice amplification device to communicate verbally to the individual. The device may be used to summon an ambulance from a remote location if the injured person is unable to reach a telephone.

As can be seen, most of the known devices are bulky in size, not portable to be located conveniently beside the victim at the rescue site, provide very limited information and are complex to operate.

Other prior devices have been developed in the past and include the Emergency Information Apparatus and Methods of U.S. Pat. No. 5,521,812 and the Instructional CD Player for providing emergency information of U.S. Pat. No. 5,668,954, the disclosures of each of which are fully incorporated herein by this reference.

SUMMARY OF THE INVENTION

A principal object of the present invention is to provide an Internet web server and method for an interactive virtual implementation and provision of instructional information in medical and other emergency situations. Another object is to provide a new form of a portable device which can be conveniently located beside a victim or near an emergency site to assist the rescuer to carry out the rescue operation.

Either implementation provides step by step instructions sequentially in response to the condition of the victim.

A particularly important aspect of the present invention, whether implemented via an Internet web server, or a physical device, is the provision of a plurality of step indicators to assist the user in determining progress with respect to completion of the instructional program. Preferably, a separate indicator such as a light, is provided for each step in the program, and as steps are completed, the corresponding indicator light is either extinguished or illuminated in a manner to provide the user with an indication that the step has been completed. During a crisis, such as a medical emergency, the persons involved can be nervous, the situation can be chaotic, there can be uncertainty as to the steps to be taken. Therefore, it is important to have something to indicate the status of the beginning and ending of the procedure as well as each step of the procedure. Such step indicators provide this important feature. Alternatively, a display of numbers (e.g., 1 through 8) can be provided with the display stepping through the numbers as steps are completed.

These objects and features are provided in the emergency information concepts of the present invention.

BRIEF DESCRIPTION OF THE DRAWINGS

These and other advantages of the present invention are best understood with reference to the drawings in which.

DETAILED DESCRIPTION OF THE PREFERRED EMBODIMENTS

Figure 1:
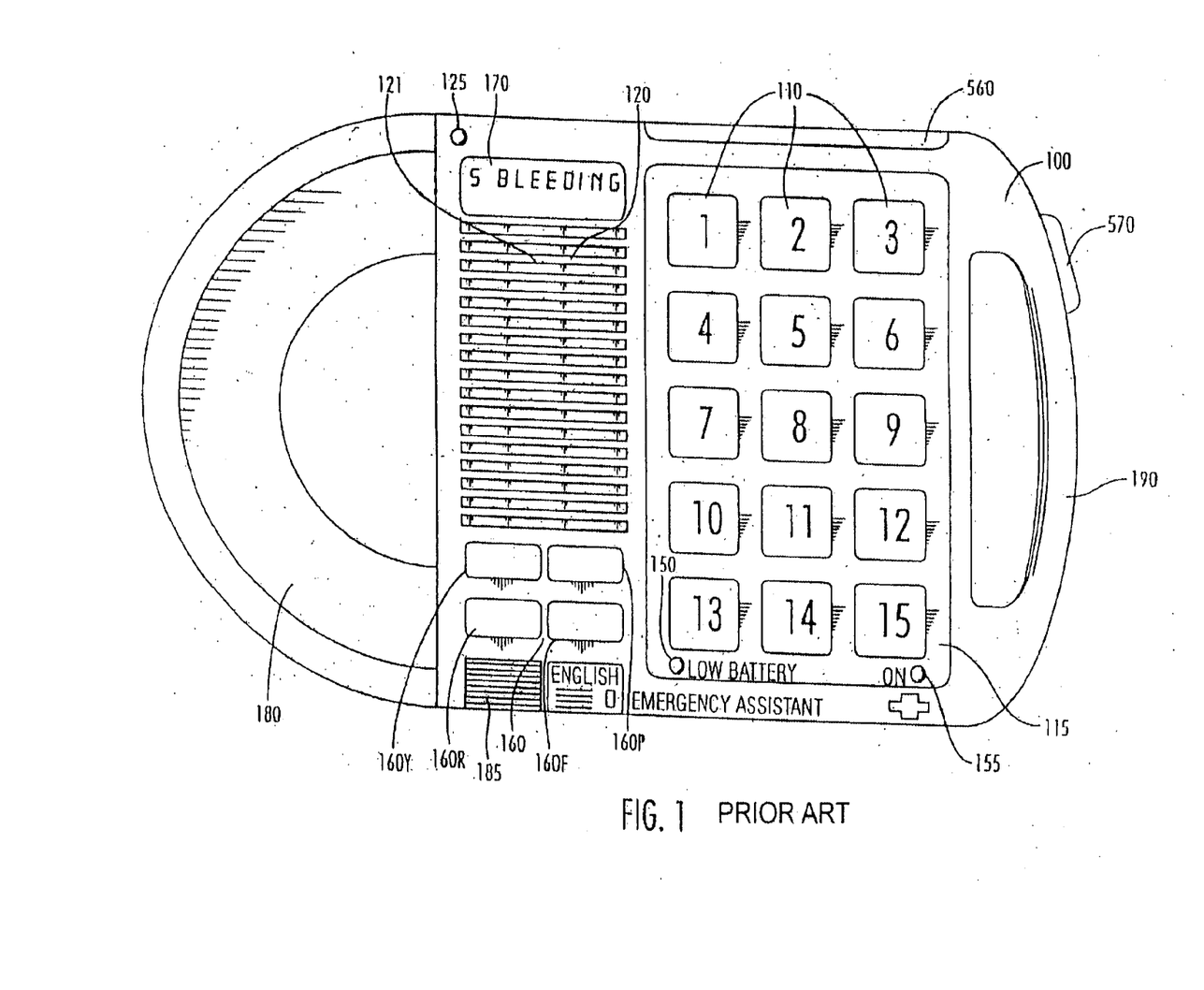
FIG. 1 is a partial elevation of an emergency information apparatus of the prior art.

Referring first to FIG. 1, there is shown a partial elevation of an emergency information apparatus of the type disclosed in U.S. Pat. No. 5,521,812 and No. 5,668,954. The external portion of the apparatus is comprised primarily of a casing 100. The casing 100 is preferably of a rigid material, such as hard plastic, PVC, or the like. In addition, the casing and the items disposed in and within the casing 100 are, together, water resistant, such that water will not seep into the internal portion of the apparatus and induce electrical shorts or corrosion. This is beneficial so that the apparatus may be used, for example, in the rain, or during fire emergencies when water is being used to dowse the fire. The bottom of the casing 100 (not shown) preferably includes shock absorbing pads, such as rubber pads embedded within the casing 100 and exposed at the outer edge of the casing 100 to reduce shock and vibration when the apparatus is set down.

On the left side of the apparatus there is a hinged compartment 180. The compartment 180 is in a closed and locked position, as shown. The compartment 180 may be opened through a release (not shown), which may be on the side or top of the apparatus as known in the art. The compartment 180 is adapted for receiving a program medium such as a compact disc (CD) (not shown). When open, the compartment 180 may receive a CD, and when closed, the compartment 180 holds the CD within the apparatus.

While a CD is one form of the program medium, other media are generally suitable. These media preferably are of a standard form and storage format, such as Data Play CD, micro cassette, floppy disk, DAT, flash memory or ROMs on a PCMCIA card.

As shown in FIG. 1, there are provided five rows of three program selectors 110. The program selectors 110 are used for selecting and thereby starting the playback of programs stored therein. The number of program selectors 110 is not critical, although several should be provided so that several emergencies may be addressed. To further control playback, there are also provided several playback selectors 160, including a pause key 160H, a reverse key 160R, a forward key 160F and a continued play key 160P. The program selectors 110 and the playback selectors 160 are preferably push buttons. The program selectors 110 and playback selectors 160 preferably are backlit.

A nearly limitless number of programs may be used with the apparatus. To accommodate this flexibility, the program selectors 110 are preferably labeled with numbers 1–15, and these numbers correspond to stored programs. Programs may include instructions relating to AIDS/HIV, bloody nose, bumps and bruises, burns, choking, CPR, dental injuries, drowning, earthquakes, electric shock, external bleeding, eye injuries, fires, fractures and dislocations, frostbite and hypothermia, heart attack, heat emergencies, insect stings and bites, internal injuries, muscle cramps, poisoning, rescue breathing, seizures and shock, stroke, spinal injuries, sprains and strains, and emergency action principles.

With each start program, there can be provided a removable overlay 115. The overlay 115 is adapted to be placed over and around the program selectors 110. The overlay 115 labels the program selectors 110 in accordance with the stored programs. Thus, by scanning the overlay 115, the user can determine which program selector 110 to press to begin a playback of a desired program. The overlay 115 is preferably a think piece of plastic, with the labels being resistant to erasure from typical use of the apparatus. The apparatus further includes a speaker 120 for playing back the audio portion of the programs stored.

Once a program selector 110 has been pressed and the selected program has begun to play, the number of the program as associated with the program selector 110 and the name of the program is displayed on a display 160. In FIG. 1, it is shown that the program number 5 related to "bleeding" has begun playback. The programs may be in multilingual audio. Preferably there is a language selector 185 in the casing.

Virtual Implementation of Information Apparatus

Figure 2:
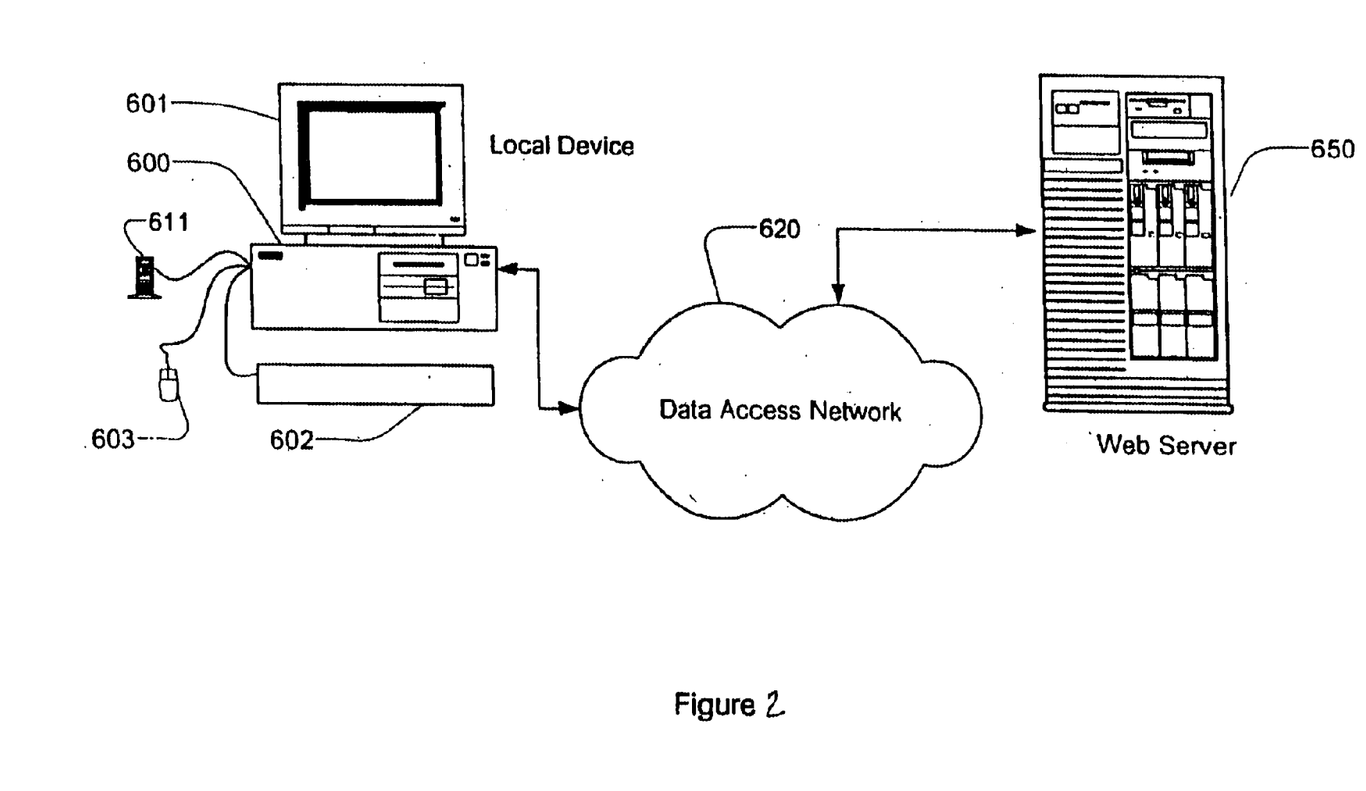
FIG. 2 is a block diagram of a network data distribution system.

Turning now to FIG. 2, there is shown a network data distribution system in which a preferred embodiment of the invention is implemented. The data distribution system includes a local device 600, a data access network 620, and a web server 650. The local device 600, the data access network 620 and the monitoring server 630 comprise the network data distribution system.

The local device 600 preferably comprises a client computer which is configured to access the web server 650 via the local access network 120. The client computer may be, for example, a PC running a Microsoft Windows operating system. The local device 600 preferably includes an output device, such as display 601, and an input device, such as keyboard 602 and/or pointing device 603 (e.g., mouse, track ball, light pen, or data glove). The local device 600 also includes a docking station 611 that allows a data access device, such as a PDA to interface with the local device 600 and exchange data.

Furthermore, the local device 100 may be any device that provides some measure of individual user interactivity with a source of web pages. For example, the local device could be an Internet appliance, network computer (NC, or an appropriately Internet-enabled device such as a PDA, mobile phone, etc.

The data access network 620 provides lower layer network support for the local device 100 to interact with the web server 650. The data access network 620 preferably comprises a common or private bi-directional telecommunications network (e.g., a public switched telephone network (PSTN), a cable-based telecommunication network, a LAN, a WAN, a wireless network), coupled with or overlayed by a TCP/IP network (e.g., the Internet or an intranet).

The web server 650 may be of the type known in the art and has the ability to serve web pages to the local device 600, as requested in the manner known in the art. It should be appreciated that the web server 650 is generic for any source of web pages available to the local device 100. Thus, for example, the web server 650 could be accessible from the Internet, or it could be a part of an intranet and represents any number of web servers.

A browser application, such as, Microsoft Internet Explorer or Netscape Navigator is preferably installed on the local device 600. When the local device 100 is connected to the web server 650 through the data access network 620, the user of the local device browses the web server 650 from the local device 600 using the browser application. The browser application itself need not be stored on the local device 600.

Figure 3:
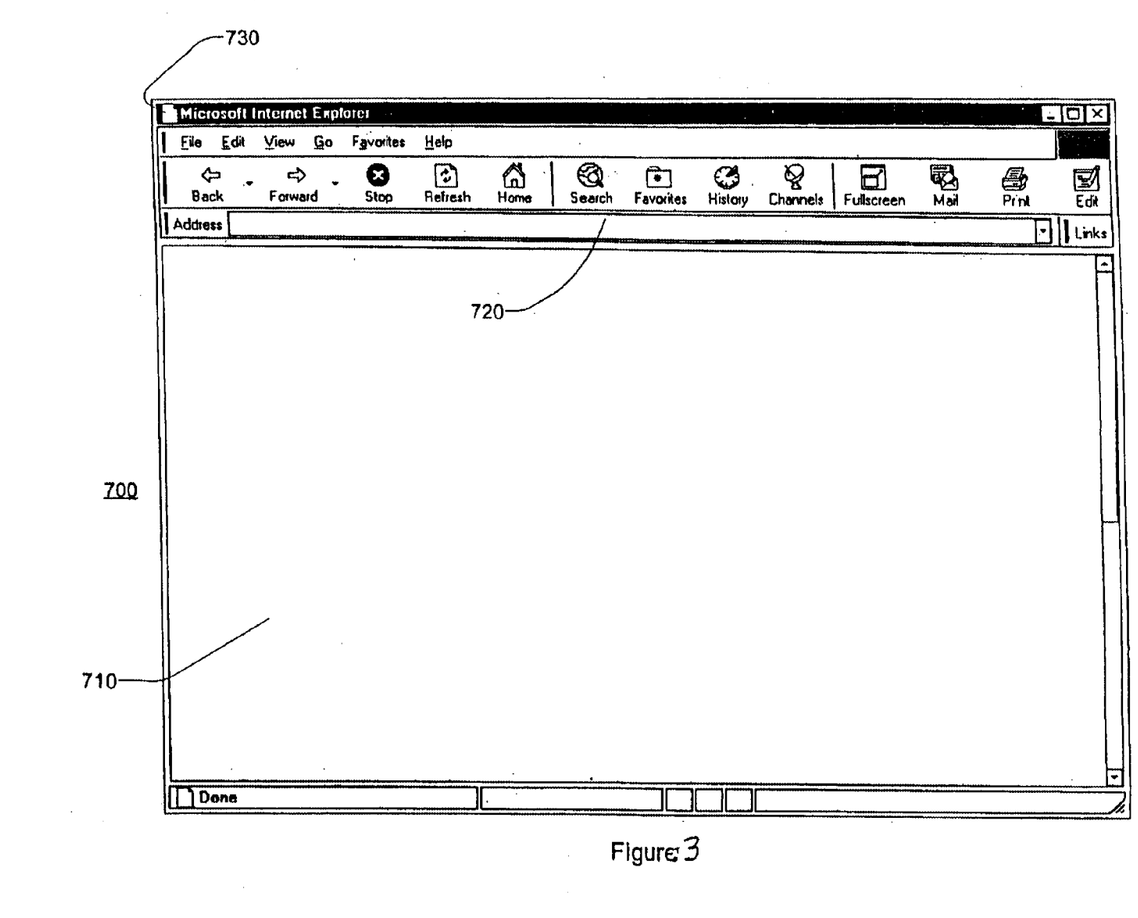
FIG. 3 shows an Internet browser window.

Referring now to FIG. 3, there is shown a browser window 700 generated by a browser application, here Microsoft Internet Explorer. The browser window 700 is familiar to those skilled in the art, so the particulars are not described further herein. Further information regarding the use of most browser applications and their technical specifications is abundantly available.

Several aspects of the browser window 700 are identified for further reference below. These aspects include a display pane 710, an address bar 720 and a title bar 730. The display pane 710 is a region of the browser window 700 wherein the browser application causes web pages received by the browser application to be displayed. The address bar 720 is another region of the browser window 700 and the browser application displays URLs in the address bay 720 corresponding to the web page currently displayed in the display pane 710. The user can also enter a URL into the address bar 720, and the browser application will attempt to load the web page or other object to which the entered URL points. The primary feature of the title bar 730 is that it displays the title of the browser application.

The web server 650 preferably includes a memory that includes one or more web pages that are associated with a virtual representation of the emergency information apparatus described above. The web server 650 downloads the web pages to the local device 600 so that a representation of the emergency information apparatus is displayed on the display device 601 within the browser display pane 710.

Figure 4:
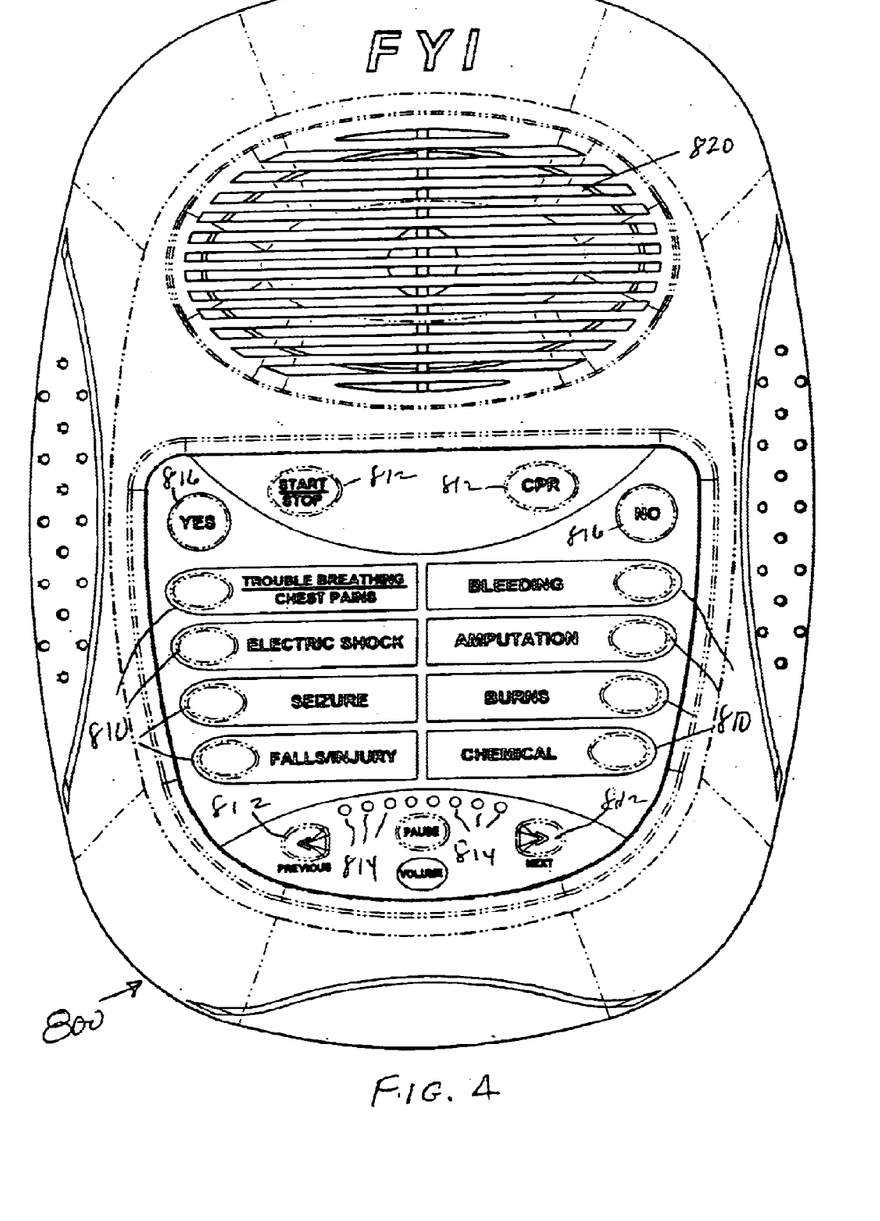
FIG. 4 shows an exemplary web page that includes a virtual representation of an information apparatus.

FIG. 4 shows an embodiment of a web page that includes a representation of a virtual emergency information apparatus 800. The virtual information apparatus 800 is preferably configured to simulate the operation of the physical apparatus described above with respect to FIG. 1. According, the web page includes several hypertext program keys 810, wherein each program key 810 is associated with a program that is stored in the web server 650. By clicking on any of the program keys 810, a user of the local device 600 causes the web server to load and initiate a program associated with the particular key 810. In a preferred embodiment, each program is associated with a set of instructions relating to an emergency medical scenario, although the programs could vary.

The virtual information apparatus 800 also includes one or more operational keys 812 that allow a user using the local device 600 to perform functions relating to the program, such as start, stop, pause, etc. In addition, the apparatus 800 includes step indicator 814 that provide a representation of the status with respect to the number of completed steps in the program, and which are described in more detail later.

With reference to FIG. 4, the virtual information apparatus also includes a representation of one or more acknowledgement keys 816 that allow a user of the local device 600 to acknowledge the completion of steps associated with a program.

Figure 5:
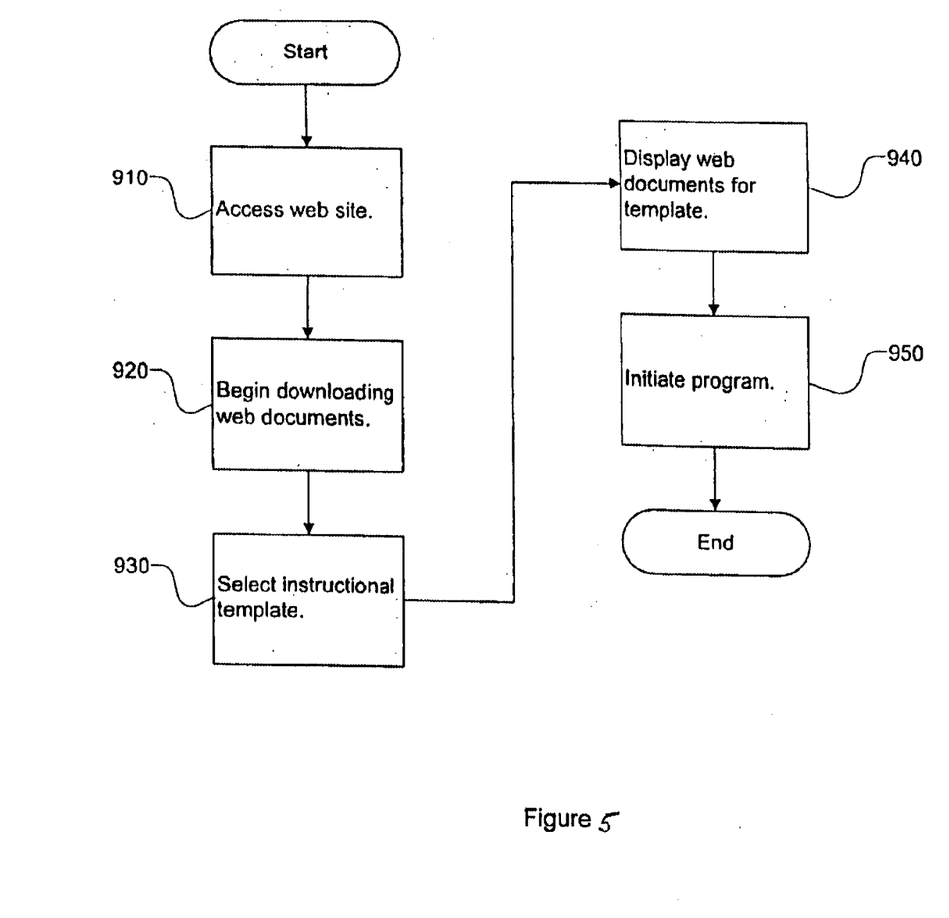
FIG. 5 is a flow chart that describes a method of providing instructional programs over the Internet in connection with a virtual information apparatus.

FIG. 5 shows a flow chart that describes process in web pages associated with the virtual emergency information apparatus are downloaded to the local device 600. The process begins when a user accesses the web server 650 using the local device 600 (step 910). In step 920, the web server 650 downloads one or more web pages to the local device 600. The web pages preferably include one or more introductory pages that allow a user to select a particular instructional template for the virtual information apparatus 800 from a list of options (step 930). For example, the user could select an instructional template associated with the provision of emergency services or provision of some category of emergency services. The templates could also be associated with other subject matter.

In any event, in step 940, after the user selects the instructional template, the web server downloads a web page in which is displayed a representation of the information apparatus 800 configured in accordance with the selected instructional template. For example, FIG. 8 shows the web page associated with the information apparatus 800 being configured to implement emergency medical instructions. The program keys 810 each include a label that indicates the particular instructional set that will be implemented when the respective key 810 is selected.

In step 950, the instruction program is initiated. The web server 650 preferably issues instructions that causes the local device 600 to play the particular program in the manner described above with respect to the physical emergency information apparatus. The user can pause, stop, play or interact with the program using the acknowledgement keys 812 and the operational keys 810.

Each program preferably comprises plural audio instruction messages that relate to steps in a procedure. In one embodiment, the procedure relates to instructional steps for dealing with an emergency medical situation. However, the procedure could also relate to instructional steps for any other type of situations for which instructional steps are appropriate. The program further comprises playback control information for directing playback of the audio step message in a predefined pattern and in accordance with operation of the operational keys 810 and acknowledgement keys 812.

In a preferred embodiment, the acknowledgement keys 812 are used interactively in response to the audio instructional steps. The user preferably selects an appropriate acknowledgement key 812 to acknowledge an audio instruction. Preferably, the program includes predetermined stop points where the program either pauses for a predetermined time or repeats an instruction until the user acknowledges completion of a step using one or more of the acknowledgement keys 812. The apparatus is preferably configured to respond to voice acknowledgements. The apparatus could be equipped with voice activation software that recognizes and responds to the voice of a user.

For example, in an emergency medical instruction program, the audio instruction may instruct the user to check a person's breathing. The program could repeat the instruction or pause playing of the next instruction until the user acknowledges that this step has been completed. Once an acknowledgment has been received, the program would then continue.

The step indicators 814 preferably assist the user in determining progress with respect to completion of the instructional program. Preferably, a separate indicator, such as a light, is provided for each step in the program. Any given program (e.g., category of medical emergency, such as bleeding, burns, seizure, etc.). For example, a "bleeding" program may involve four steps, a "seizure" program eight steps, and the like. When one of the programs is selected, all of the lights can be illuminated, such as illuminated green, so that the operator can readily see that there are four, five, six or more steps as the case may be. As the steps are completed, the corresponding indicator light is either extinguished or illuminated, or illuminated in a different color, to provide the user an indication that the step has been completed. The indicator could also blink or flash during the pendency of a particular step. The step indicators 814 thus provide the user with a visual status and summary relating to the progress of the particular program that is being played.

In a preferred embodiment, the docking station 611 can be used to transfer one or more programs and virtual representations of the information apparatus to a PDA, such as a Palm Pilot. The PDA may then be used to implement the instructional program. For example, the user could dock the PDA to the docking station 611 and then download a virtual information apparatus into the memory of the PDA. Thereafter, the functionally provided in the web page representation of the virtual information apparatus would be available directly on the PDA, preferably via a touch screen on the PDA. Preferably, audio files in the form of voice instructions are downloaded to the PDA as part of the instructional program and virtual information apparatus. The PDA is also configured to accept voice instructions from the user from a microphone positioned on the PDA. Alternatively, the programs can be stored or embedded in the computer (e.g., in the hard drive) or PDA memory and be accessible via an emergency icon.

Physical Device

The virtual apparatus of the present invention as shown in FIG. 4 also can be implemented in a physical device of the nature earlier described in connection with FIG. 1, but further includes the step indicators 814 in the physical device operating in the same manner as described above and for the same purposes. Thus, the concepts of the present invention can be implemented in the form of a virtual device through a network data distribution system and the Internet, or via other communications systems, and can as well be implemented in a physical device like that shown in FIG. 4.

Figure 6:
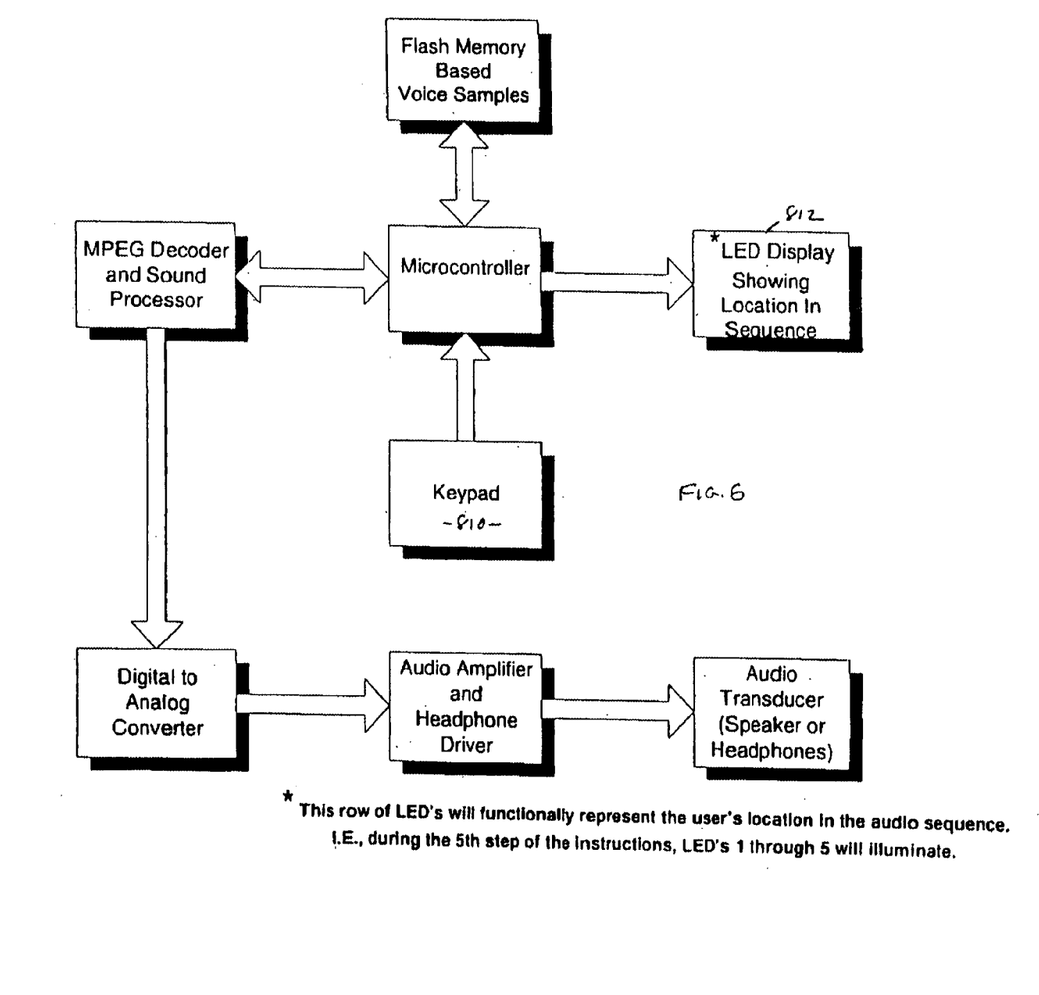
FIG. 6 is a block diagram of a hardware implementation device according to the present invention.

This device typically is battery powered and includes a speaker 820 (FIG. 4) for providing audible instructions and includes an internal system as shown in FIG. 6 with a microcontroller interconnected with the keypad 810 and the step indicators 812 to appropriately cause illumination or extinguishing of the lights (e.g., LED's). The programs preferably are stored in a flash memory, and the other components of the system shown in FIG. 6 provide the audio information.

As noted earlier, the steps can be indicated via a display of numbers which are stepped through as program steps are completed, for either or both of the virtual system or portable device.

While embodiments of the present invention have been shown and described, various modifications may be made without departing from the scope of the present invention, and all such modifications and equivalents are intended to be covered.

What is claimed is:

1. Computer readable software code stored on a web document server, the web server being part of a client server network, the computer readable software code including a set of instructions for causing the web server to download a web document to a client device, the web document including a virtual representation of an emergency information apparatus including one or more individually selectable program selectors for selecting a specific program to be played, wherein each program comprises plural audio instruction messages comprising steps in a procedure, and playback control information for directing playback of the audio step messages in a predefined pattern and in accordance with operation of the playback selectors, the playback control information including the location of each audio instruction message on the web server and the order of playback of the audio instructions within the program.

2. Software code as claimed in claim 1 wherein the virtual representation includes a series of step indicators to assist the user in determining progress with respect to completion of an instructional program.

3. A software code as in claim 2 wherein the step indicators are all illuminated at the commencement of the program and change as each step in the program is complete.

4. A software code as in claim 2 wherein the step instructions comprise numbers provided on a display.

5. A compact portable information apparatus comprising a plurality of program keys, each key being associated with an instructional program, such as an emergency medical scenario, and wherein depression of a key initiates a series of steps of the program, and a plurality of step indicators to assist the program user in determining progress of completion of the instructional program and steps thereof, the step indicators comprising a plurality of illumination members which change in illumination as each step in the program is completed.

6. Apparatus as in claim 5 wherein the plurality of step indicators are all illuminated upon initiation of a program, and sequentially changed as respective steps of the program are completed.

7. Apparatus as in claim 5 wherein the apparatus further includes acknowledgement keys to allow the user to acknowledge completion of steps associated with a program.

8. Apparatus as in claim 5 wherein the step indicators comprise numbers provided on a display.

9. A virtual information apparatus comprising a plurality of program keys, each key being associated with an instructional program, such as an emergency medical scenario, and wherein use of a key initiates a series of steps of the program, and a plurality of step indicators for each program to assist the program user in determining progress of completion of the respective instructional program and steps thereof, the step indicators comprising a display of a plurality of illumination members which change as each step in the program is completed.

10. Virtual apparatus as in claim 9 wherein the step indictors comprise lights that are all illuminated upon initiation of a program, and sequentially changed as respective steps of the program are completed.

11. Virtual apparatus in claim 9 wherein the step indicators comprise a display of sequential members indicating each respective step.

12. Apparatus comprising a plurality of program keys, each key being associated with an instructional program, such as an emergency medical scenario, and wherein use of a key initiates a series of steps of the program, and a plurality of step indicators for each program to assist the program user in determining progress of completion of the respective instructional program and steps thereof, the step indicators comprising a display of a plurality of illumination members which change as each step in the program is completed.

13. Apparatus as in claim 12 wherein the step indicators comprise lights that are all illuminated upon initiation of a program, and sequentially changed as respective steps of the program are completed.

14. Apparatus as in claim 12 wherein the step indicators comprise a display of sequential members indicating each respective step.

15. A virtual information method using a plurality of program keys, each key being associated with an instructional program, such as an emergency medical scenario, and wherein use of a key initiates a series of steps of the program, and generating a plurality of step indicators for each program to assist the program user in determining progress of completion of the respective instructional program and steps thereof, the step indicators comprising a display of a plurality of illumination members which change as each step in the program is completed.

16. Virtual apparatus as in claim 15 wherein the step indicators comprise lights that are all illuminated upon initiation of a program, and sequentially changed as respective steps of the program are completed.

17. Virtual apparatus in claim 15 wherein the steps indicators comprise a display of sequential members indicating each respective step.

18. An information method using a plurality of program keys, each key being associated with an instructional program, such as an emergency medical scenario, and wherein use of a key initiates a series of steps of the program, and generating a plurality of step indicators for each program to assist the program user in determining progress of completion of the respective instructional program and steps thereof, the step indicators comprising a display of a plurality of illumination members which change as each step in the program is completed.

19. Virtual apparatus as in claim 18 wherein the step indicators comprise lights that are all illuminated upon initiation of a program, and sequentially changed as respective steps of the program are completed.

20. Virtual apparatus in claim 18 wherein the step indicators comprise a display of sequential members indicating each respective step.

21. A virtual information apparatus comprising a plurality of program keys, each key being associated with an instructional program, such as an emergency medical scenario, and wherein use of a key initiates a series of steps of the program, and a plurality of step indicators to assist the program user in determining progress of completion of the instructional program and steps thereof, the step indicators comprising a display of a plurality of illumination members which change as each step in the program is completed, and wherein the step indictors comprise lights that are all illuminated upon initiation of a program, and sequentially changed as respective steps of the program are completed.

22. A virtual information apparatus comprising a plurality of program keys, each key being associated with an instructional program, such as an emergency medical scenario, and wherein use of a key initiates a series of steps of the program, and a plurality of step indicators to assist the program user in determining progress of completion of the instructional program and steps thereof, the step indicators comprising a display of a plurality of illumination members which change as each step in the program is completed, and wherein the step indicators comprise a display of sequential members indicating each respective step.

23. Apparatus comprising a plurality of program keys, each key being associated with an instructional program, such as an emergency medical scenario, and wherein use of a key initiates a series of steps of the program, and a plurality of step indicators to assist the program user in determining progress of completion of the instructional program and steps thereof, the step indicators comprising a display of a plurality of illumination members which change as each step in the program is completed, and wherein the step indicators comprise lights that are all illuminated upon initiation of a program, and sequentially changed as respective steps of the program are completed.

24. Apparatus comprising a plurality of program keys, each key being associated with an instructional program, such as an emergency medical scenario, and wherein use of a key initiates a series of steps of the program, and a plurality of step indicators to assist the program user in determining progress of completion of the instructional program and steps thereof, the step indicators comprising a display of a plurality of illumination members which change as each step in the program is completed, and wherein the step indicators comprise a display of sequential members indicating each respective step.

25. A virtual information method using a plurality of program keys, each key being associated with an instructional program, such as an emergency medical scenario, and wherein use of a key initiates a series of steps of the program, and generating a plurality of step indicators to assist the program user in determining progress of completion of the instructional program and steps thereof, the step indicators comprising a display of a plurality of illumination members which change as each step in the program is completed, and wherein the step indicators comprise lights that are all illuminated upon initiation of a program, and sequentially changed as respective steps of the program are completed.

26. A virtual information method using a plurality of program keys, each key being associated with an instructional program, such as an emergency medical scenario, and wherein use of a key initiates a series of steps of the program, and generating a plurality of step indicators to assist the program user in determining progress of completion of the instructional program and steps thereof, the step indicators comprising a display of a plurality of illumination members which change as each step in the program is completed, and wherein the steps indicators comprise a display of sequential members indicating each respective step.

27. An information method using a plurality of program keys, each key being associated with an instructional program, such as an emergency medical scenario, and wherein use of a key initiates a series of steps of the program, generating a plurality of step indicators to assist the program user in determining progress of completion of the instructional program and steps thereof, the step indicators comprising a display of a plurality of illumination members which change as each step in the program is completed, and wherein the step indicators comprise lights that are all illuminated upon initiation of a program, and sequentially changed as respective steps of the program are completed.

28. An information method using a plurality of program keys, each key being associated with an instructional program, such as an emergency medical scenario, and wherein use of a key initiates a series of steps of the program, generating a plurality of step indicators to assist the program user in determining progress of completion of the instructional program and steps thereof, the step indicators comprising a display of a plurality of illumination members which change as each step in the program is completed, and wherein the step indicators comprise a display of sequential members indicating each respective step.

29. Computer readable software code stored on a web document server, the web server being part of a client server network, the computer readable software code including a set of instructions for causing the web server to download a web document to a client device, the web document including interactive instructional information and including one or more individually selectable program selectors for selecting a specific program to be played, wherein each program comprises plural audio instruction messages comprising steps in a procedure, and playback control information for directing playback of the audio step messages in a predefined pattern and in accordance with operation of the playback selectors, the playback control information including the location of each audio instruction message on the web server and the order of playback of the audio instruction within the program.

30. Software code as claimed in claim 29 wherein the virtual representation includes a series of step indicators to assist the user in determining progress with respect to completion of an instructional program.

31. A software code as in claim 30 wherein the step indicators are all illuminated at the commencement of the program and change as each step in the program is complete.

32. Computer readable software code stored on a web document server, the web server being part of a client server network, the computer readable software code including a set of instructions for causing the web server to download a web document to a client device, the web document including situations for which instructional steps are appropriate and including one or more individually selectable program selectors for selecting a specific program to be played, wherein each program comprises plural-audio instruction messages comprising steps in a procedure, and playback control information for directing playback of the audio step messages in a predefined pattern and in accordance with operation of the playback selectors, the playback control information including the location of each audio instruction message on the web server and the order of playback of the audio instructions within the program.

33. Software code as claimed in claim 32 wherein the virtual representation includes a series of step indicators to assist the user in determining progress with respect to completion of an instructional program.

34. A software code as in claim 33 wherein the step indicators are all illuminated at the commencement of the program and change as each step in the program is complete.

\* \* \* \* \*